United States Patent [19]

Baczkowski

[11] 4,257,680

[45] Mar. 24, 1981

[54] MIRROR ASSEMBLY FOR PATIENTS WITH PERSONAL HYGIENE PROBLEMS

[76] Inventor: Joseph S. Baczkowski, 207 Piper, Detroit, Mich. 48215

[21] Appl. No.: 63,713

[22] Filed: Aug. 6, 1979

[51] Int. Cl.³ .............................................. G02B 7/18
[52] U.S. Cl. .................................... 350/298; 128/21
[58] Field of Search ..................... 128/21; 350/98, 298

[56] References Cited

U.S. PATENT DOCUMENTS

| 1,389,053 | 8/1921 | King | 350/298 |
| 2,979,990 | 4/1961 | Alexander | 350/298 |
| 3,276,416 | 10/1966 | Dirks et al. | 350/98 X |
| 3,411,842 | 11/1968 | Levy | 350/298 |

FOREIGN PATENT DOCUMENTS 849508 11/1939 France ..................................... 350/298

Primary Examiner—F. L. Evans

[57] ABSTRACT

A mirror assembly for use by patients having ostomies or the like which are located in places on the body that cannot be seen directly by the patient comprises a mirror member, a support plate, and mounting elements for adjustably mounting the mirror on the support plate, the support plate being adapted to fit on the leg of the patient and be strapped to it whereby the patient's hands are freed and the mirror may be adjusted in position by movement of the leg.

6 Claims, 8 Drawing Figures

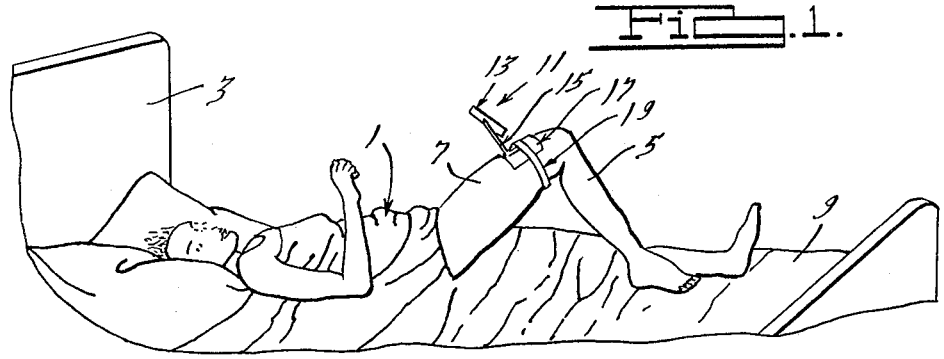
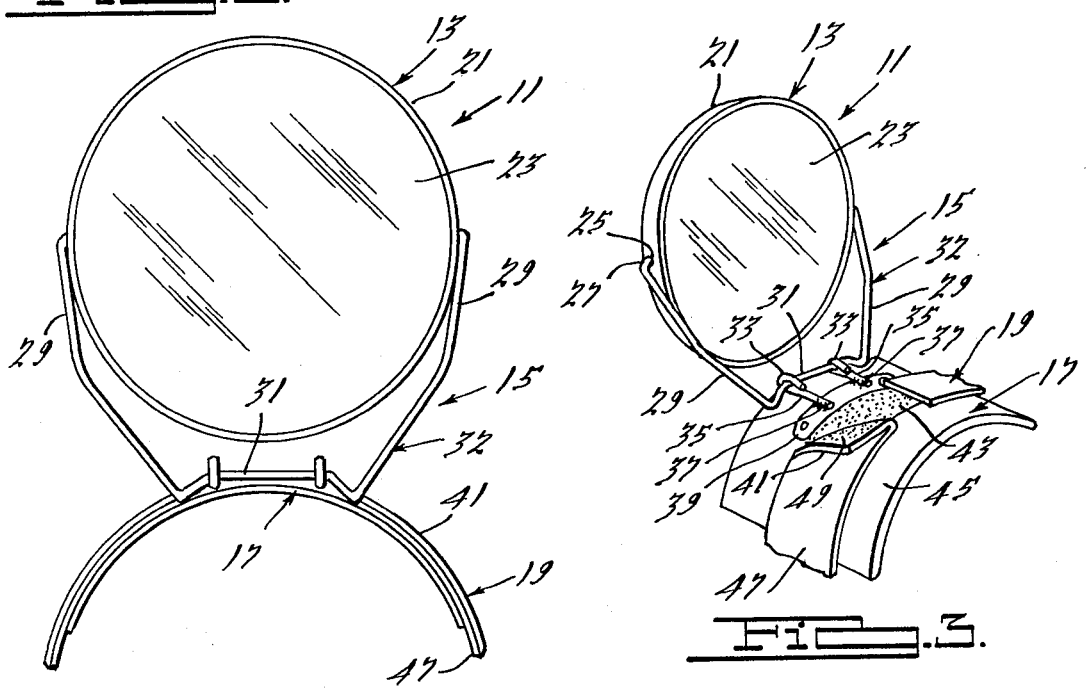

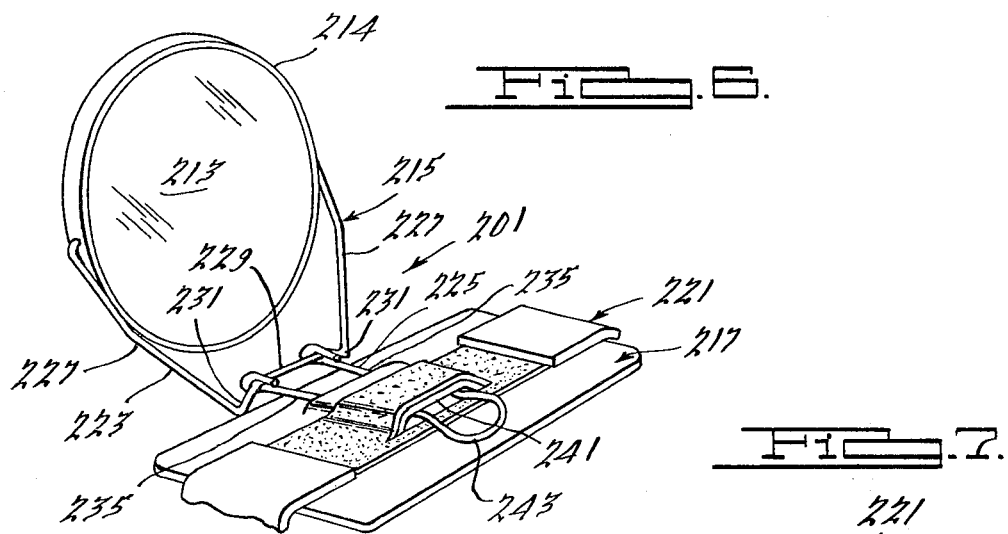
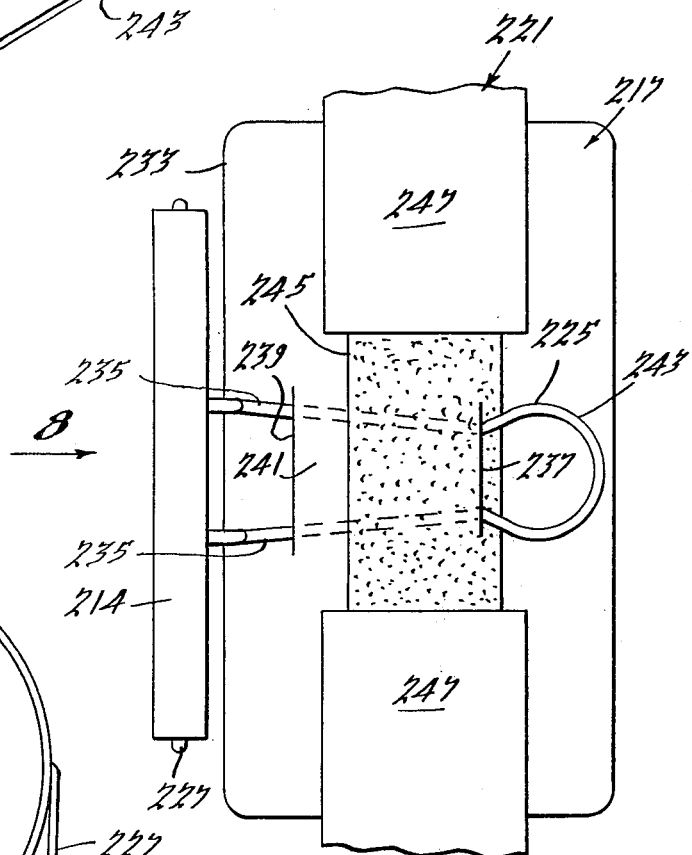
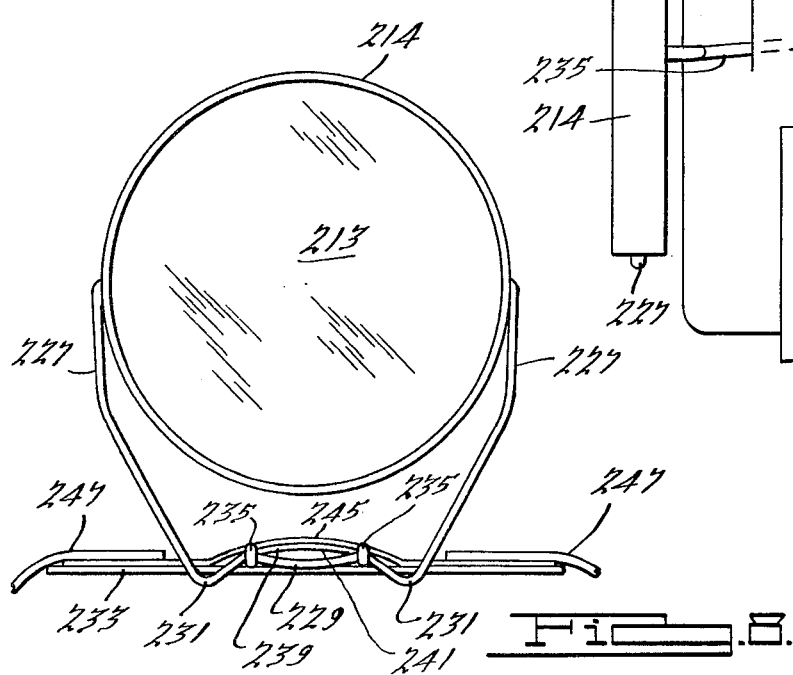

MIRROR ASSEMBLY FOR PATIENTS WITH PERSONAL HYGIENE PROBLEMS

BACKGROUND OF THE INVENTION

There are an estimated one and a half million people in the United States today that have special, personal hygiene problems (such as changing dressings, etc.) due to ostomies or the like. An ostomy is a general term referring to any operation in which an artificial opening is formed between one or more hollow organs and the abdominal wall for discharge of intestinal contents or of urine. These operations are performed because of gastrointestinal, urological or proctological problems arising from disorders such as cancer, spinal cord injury, cerebral palsy, multiple sclerosis, colitis, ulcers, etc. The patients utilize special collecting appliances in the form of a pouch that is attached to the stoma or mouth of the opening and which must be carefully and frequently changed.

There are also an estimated one million people that suffer bowel and bladder dysfunction as a result of paralysis from accidents or diseases affecting the spinal cord. These people and others may utilize special equipment in the form of catheters, drainage bags, suppositories, and enemas in order to stimulate discharge or to collect uncontrollable discharge.

Fortunately, most of these two and a half million people suffering from this type of problem are independent in caring for themselves. However, there are many who cannot do this because of one basic problem—visualizing either the urogenital area, the anus, or the stoma which is usually located low on the abdominal wall. This problem may arise because of a protruding abdomen, wrinkled or folded skin, large breasts, inability to flex the spine, weakness in maintaining certain positions, poor balance, etc. Any of these may be such a handicap that the patient must have assistance in performing his very personal functions and hygiene routine. Cleanliness is very important to minimize the chance of infection and skin irritations and is very difficult when the area cannot be seen.

Visibility is most important in using toileting equipment because many patients have decreased sensation and cannot simply feel what they must do. Due to the nature of their affliction, many people who use special equipment for toileting are unable to stand and therefore cannot utilize a wall mirror if one is available. Hand mirrors help with visibility but eliminate the use of one hand. Supine or side lying positions are often recommended for changing an appliance or inserting a suppository since these are stable positions that allow the person to relax and gravity to act on the abdomen and its contents, thus affording a cleaner and therefore safer procedure. However, these positions also afford poor visibility.

BRIEF SUMMARY OF THE INVENTION

It is the purpose of this invention to provide a device that will enable patients to personally and privately attend to use of ostomy devices and attend to problems involved with personal cleanliness, hygiene, toileting, dressings, suppositories, catheters, etc., associated with ostomies and other disorders having similar personal consequences.

The invention accomplishes the purpose by means of a mirror assembly that is designed to free both hands of the patient for use in holding the ostomy appliance or dealing with a hygienic process and that also enables him to see portions of his body that cannot be seen directly. The mirror assembly comprises a mirror member which may be fastened to the lower thigh of the patient's leg. The mirror is attached by means of mounting elements on a plate member that fits the top of the patient's thigh. A flexible attaching element secured to the plate is adapted to extend around the patient's leg and firmly secure the plate and thus the mirror to the leg.

DESCRIPTION OF THE DRAWINGS

FIG. 1 is a perspective view of a patient utilizing the mirror assembly of this invention.

FIG. 2 is an end elevation partly broken away of the mirror assembly shown in FIG. 1.

FIG. 3 is a perspective view of the mirror assembly of FIGS. 1 and 2 and shows the flexible strap attached to the support plate.

FIG. 4 is a perspective view of the mirror assembly of FIGS. 1 thru 3 showing the mirror in a folded position suitable for packing in a purse or luggage.

FIG. 5 is a perspective view of a modified form of mirror assembly.

FIG. 6 is a perspective view of another form of the invention with the strap partly broken away.

FIG. 7 is a plan view, with the straps broken away, of the mirror assembly of FIG. 6.

FIG. 8 is an elevation taken from the left of FIG. 7.

DETAILED DESCRIPTION OF THE INVENTION

In FIG. 1, a patient 1 is lying in a bed 3 and has a leg 5 partly elevated so that the thigh 7 is located above the mattress 9 and the leg 5 may be moved about to vary the position of a mirror assembly 11 that embodies the present invention. The mirror assembly 11 has a mirror member 13 which is adjustably mounted by means of mounting elements 15 on a support plate 17. The plate 17 is curved to fit the top convex surface of the thigh 7 and carries a strap 19 that extends around the back of the leg 5 and has means whereby it may be tightened to securely mount the plate 17 on the thigh 7.

The angular position of the mirror member 13 may be adjusted since it is pivoted on a substantially horizontal axis and this adjustment along with the wide range of movements that the patient may make with the leg 5 will enable the patient to see virtually any part of the front of her body. Thus, the patient can see any ostomy appliance or catheter or condom, as well as the affected area of the body and since the patient's hands are not used to hold a mirror, they can be used in private, personal care of the ostomic or other area.

Referring to FIGS. 2 thru 4 for a more detailed description of the mirror assembly 11, the mirror member 13 has an outer annular rim 21 which surrounds and supports the reflecting surfaces 23 on opposite sides of a mirror plate within the rim. The rim 21 is provided with openings 25 at opposite ends of a substantially horizontal diameter and these receive the inturned ends 27 at the free ends of wire arms 29 that are a part of the supporting elements 15. The arms 29 extend from a base section 31 and with it form a substantially U-shaped configuration 32. The base section 31 is held by reversely bend ends 33 on a pair of horizontal wire bars 35 which are welded or brazed at their other ends, as seen at 37, to a bracket 39 that is shaped to fit on the top of the support plate 17. The bracket 39 and the bars 37 and the U-shaped member 32 with arms 29 all form mounting elements for the mirror member 13; and it will be seen that the U-shaped section is hinged about the axis of the base 31 which is squeezed by the reversely bent ends 33. FIG. 3 shows the mirror member 13 in an operative position; while FIG. 4 shows the assembly pivoted about the section 31 to an inoperative position wherein the mirror 13 fits against the upper face of the support plate 17 for storage or traveling purposes.

The support plate 17 is preferably made from a stiff plastic sheet of suitable size, for example a piece 4"×6" and 0.125" thick. The material sold under the trademark "Kydex" is suitable. It is provided with a concave curvature to accommodate and fit the convex upper surface of the thigh 7.

The support plate 17 and thus the entire mirror assembly 11 is held on to the thigh 7 by means of a flexible strap 19 having at least one end 41, that is easily connectable and disconnectable to enable the strap to be tightened, loosened or disconnected. A preferable construction of the end 41 of the strap 19 comprises the use of material known under the trademark "Velcro". For this purpose a layer 43 of Velcro material is fastened by adhesive or the like to the top surface 45 of the support plate 17 as seen in FIG. 3. The long flexible strap portion 47 of the strap 19 has Velcro material on its inside face as shown at 49. Thus, when the portion 47 is extended around the bottom of the patient's thigh 7, the ends may be pressed against layer 43 so that they will be held in place by the inter-engagement of the interlocking Velcro fingers. The radius of the loop described by the strap 19 may be easily adjusted to fit the leg tightly. The support plate 17 has sufficient friction so that it does not pivot about the thigh 7 and therefore provides a stable base for the mirror member 13.

Referring to a modified form of mirror assembly 101 shown in FIG. 5, there is a rimmed mirror member 103 that is substantially identical to the configuration 32. The bottom section 107 of the holder 105 is squeezed between reversely bent end sections 109 (corresponding to sections 33) on a U-shaped wire anchor element 111. The assembly of mirror 103, holder 105, and element 111 is available on the open market as a "cosmetic mirror". The element 111 is fusion bonded (welding, brazing, soldering, etc.) or otherwise affixed to an achor plate 113. The plate 113 may be secured by rivets 115 to a support plate member 117 (preferably a synthetic, non-metallic, plastic material) which corresponds to but is somewhat different than the curved plate 17 previously described. A rivet 119 having an end bent over the bight of the wire element 111 also serves to secure it to the plate 117.

In contrast to the support plate 17, the support plate 117 is substantially flat. It is, however, relatively thin and flexible so that it can be shaped to the outer surface of the patient's leg. It is secured to the leg by means of an attaching means 121, corresponding to strap 19. The attaching means 121 includes a flexible strap 125 that has Velcro on its inside face so that its ends may be placed against a Velcro section 123 to provide a means for tightly holding the plate 117 on the leg and in a position (not shown) wherein it is curved to suit the contour of the leg.

The mirror 103 may be pivoted on the U-shaped holder 105 as well as hinged around the section 107 so that a considerable degree of mirror adjustment is possible relative to the plate 117. In addition, the patient can move her leg into many different positions and also adjust the location of the mirror assembly 101 on her leg, so that ultimately she will be able to maintain the desired image in the mirror.

In FIGS. 6 to 8 the mirror assembly 201 includes a mirror member 213 with an outer rim 214 that receives mounting member 215 that serve as means to adjustably mount the mirror on a bendable support plate 217 similar to the plate 117, e.g., a 4"×6" sheet of 0.060" thick low density polyethylene material. The plate 217 carries a strap 221 that serves to securely mount the assembly on a patient's thigh.

Mounting member 215 comprises a pair of generally U-shaped elements 223 and 225. The element 223 is basically the same as the corresponding structure shown in FIGS. 2–4 and comprises side legs 227 interconnected by a bottom portion 229. The outer ends of the side legs 227 are bent inwardly and fit inside appropriate holes located in the rim 214 along a diameter of the mirror 213. Since the member 223 is preferably formed of wire it has a certain elasticity and spring-like quality whereby the legs 227 press themselves against the rim 214 to prevent inadvertant removal. The base section 229 of the element 223 has a central section that is offset upwardly or toward the rim 213 so that the outer ends of the base section are extended downwardly as seen at 231 to form abutments or shoulders engagable with the side edge 233 of the plate 217 to help hold the legs 227 perpendicular to plate 217 while allowing the mirror 213 to be folded over on top of the plate (see FIG. 4) when desired.

The U-shaped element 225 serves as a base or anchor and has legs 235 with ends that are rebent around the central section of the bottom 229 of element 223 to provide a hinge type joint between the element 223 and 255. The element 225 is basically flat or planar and the offset in the bottom section 229 is dimensioned so that at least a portion of it will lie on top of the plate 217 when the sections 231 abut the edge 233.

In this form of the invention, the plastic material of which the plate 217 is formed is slit as indicated by the parallel lines 237 and 239 which extend at right angles to the length of the element 225, the slit 239 preferably being longer than 237. The slits plus the flexible nature of the plastic material of which the plate 217 is composed enables the area of the plate defined by the two slits to be offset at 241 in a direction perpendicular to the plane of plate 217 to expose slots which will receive the U-shaped member 225. The inherent resilience of the plate 217 causes the offset plate section 241 to tightly press against the U-shaped element 225 thereby holding the U-section 243 and end portions of the legs 235 tightly against the top surface of the plate 215.

As in the preceding embodiments a strip of Velcro material 245 is glued or otherwise suitably attached to the top of the plate 217 and may extend over the offset 241. The strap 221 has Velcro material on its end portions 247 so that they can be pressed against the connecting Velcro section 245 to provide a means for easily connecting and disconnecting the strap and enabling it to be set at a desired diameter.

Thus, it will be seen that the mirror assemblies of the invention may be easily attached to and adjusted on a patient's leg and that after attachment the patient's hands are free. While it is mounted on the leg, the position of the mirror assembly may also be adjusted even further by movement of the leg. The mirror may be folded against the mounting plate for storage or travelling.

Modifications in the specific structure shown may be made without departing from the spirit and scope of the invention.

I claim:

1. A mirror assembly for adjustable mounting on the thigh of a human patient and when mounted being movable with the thigh, comprising a sustantially rectangular thin elastically bendable support plate, a mirror, means mounting the mirror on the plate for pivotal adjustment about an axis transverse to the length of the plate, strap means for removably but tightly securing the plate to the thigh of a patient, when mounted on said thigh said plate being elastically curved about an axis normal to its length whereby it substantially conforms temporarily to the curvature of the thigh.

2. A mirror assembly as set forth in claim 1 wherein said strap means include Velcro fasteners for holding strap portions in desired positions.

3. A mirror assembly as set forth in claim 1 wherein means for mounting the mirror includes an anchor plate secured to the support plate and a wire element fusion bonded to the anchor plate.

4. A mirror assembly as set forth in claim 1 wherein means mounting said mirror includes an anchor element and said support plate includes a centrally located flexible portion that may be elastically offset from the plane of the plate to provide openings to receive said anchor element, said anchor element extending through said openings and said flexible offset portion serving to elastically clamp said anchor element to said support plate.

5. A mirror assembly as set forth in claim 1 wherein said mounting means comprises a U-shaped wire holder having ends fitting in sides of the mirror to provide a pivot axis for the mirror, and a hinge socket means affixed to the plate and tightly but movably receiving the bottom of the U-shaped holder, said bottom being angularly movable in said socket means whereby the holder may be hinged against the plate for storage.

6. A mirror assembly to be mounted on the leg of a human patient comprising a support plate bendable into conformity with a patient's thigh, a mirror, and means for adjustably mounting a mirror on the support plate so that the plane of the mirror is substantially parallel to the length of the plate, said means comprising a first U-shaped member having a bottom section and side legs, said mirror being pivotably supported on said side legs, said bottom section including portions engagable with an edge of said plate, a second U-shaped member having a bottom section and side legs, the ends of the side legs of said second U-shaped member being pivotably secured to the bottom section of the first U-shaped member, said plate having a slit portion formed in it whereby an area of the plate defined by said slit portion may be offset from and separated from the remainder of the plate but is urged by the inherent resiliency of the plate toward a co-planar position, said second U-shaped member being projected through the space formed between the slit portion and the balance of the plate and being resiliently held in position by said slit portion.

* * * * *